United States Patent [19]

Angstadt

[11] 4,034,047

[45] July 5, 1977

[54] PROCESS FOR CATALYTIC OXIDATION OF OLEFINS TO FORM HYDROPEROXIDES

[75] Inventor: Howard P. Angstadt, Media, Pa.

[73] Assignee: Suntech, Inc., St. Davids, Pa.

[22] Filed: Feb. 17, 1976

[21] Appl. No.: 656,055

Related U.S. Application Data

[60] Division of Ser. No. 524,912, Nov. 18, 1974, abandoned, which is a continuation-in-part of Ser. No. 853,547, Aug. 27, 1969, abandoned.

[52] U.S. Cl. .................... 260/610 B; 260/618 C; 260/599; 260/590 R; 252/429 C; 252/431 N
[51] Int. Cl.$^2$ ................ C07C 29/00; C07C 179/00
[58] Field of Search .......... 260/610 B, 618 C, 599, 260/590; 252/429 C, 431 N; 526/48

[56] References Cited

UNITED STATES PATENTS

| 2,751,418 | 6/1956 | Enos ............................ 260/610 B |
| 3,200,100 | 8/1965 | Dennstedt ...................... 260/85.5 |
| 3,301,905 | 1/1967 | Riemenschneider et al. ... 260/610 B |

Primary Examiner—Winston A. Douglas
Assistant Examiner—John F. Niebling
Attorney, Agent, or Firm—Donald R. Johnson; J. Edward Hess; Stanford M. Back

[57] ABSTRACT

Polymeric complexes formed between a thermally-condensed polyacrylonitrile polymer and transition metal salts, including rare earth metals, have been found to be effective catalysts for the oxidation of compounds containing activated carbon-hydrogen bonds such as olefins, or secondary and tertiary alkylaromatics, to form valuable oxidation products, particularly hydroperoxides or their decomposition products.

13 Claims, No Drawings

PROCESS FOR CATALYTIC OXIDATION OF OLEFINS TO FORM HYDROPEROXIDES

CROSS-REFERENCE TO RELATED APPLICATIONS

This is a division of application Ser. No. 524,912, filed Nov. 18, 1974, now abandoned, which in turn is a continuation-in-part of U.S. Ser. No. 853,547, filed Aug. 27, 1969, now abandoned.

This application is related to one following applications:

| Serial No. | Applicant | File Data |
|---|---|---|
| 772,421 | Angstadt et al | 10/31/68 |
| 526,036 | Angstadt et al | 11/21/74 |
| 524,910 | Angstadt | 11/18/74 |
| 524,911 | Angstadt | 11/18/74 |
| 529,548 | Angstadt | 11/20/74 |

The entire disclosure of all of the above six applications is hereby incorporated herein by reference.

BACKGROUND OF THE INVENTION

This invention relates to a novel process and catalyst for the oxidation of compounds containing activated carbon-hydrogen bonds, particularly those compounds containing activated methylene and methine groups, to form various oxidation products, particularly hydroperoxides, or the decomposition products thereof, i.e., alcohols, aldehydes, ketones or the like, or mixtures thereof. More particularly, this invention is directed to the use of complexes formed by reacting certain metal salts with a thermally-condensed polyacrylonitrile polymer as oxidation catalysts in the aforesaid process, and to those complexes per se formed between such polymers and transition metal salts, including lanthanide metal salts. By the term "lanthanide metal salts" is meant that metal lanthanum as well as other metals in this series. By the term "activated carbon-hyrogen bonds" is meant those hydrogen-containing carbon atoms such as methylene or methine groups which are adjacent certain activating groups discussed more fully hereinbelow.

The oxidation of activated carbon components defined above, as for example aromatic compounds, is already well known in the art. Thus, for example, it is known that tertiary alkylaromatics such as cumene can be auto-oxidated very slowly to form cumyl hydroperoxide when air or oxygen is rapidly passed through cumene warmed to about 80° C. Also, Canadian Pat. No. 510,517 teaches that the rate of oxidation of cumene can be enhanced when carried out in the presence of alkali or alkaline earth metal oxides of hydroxides, or in the presence of salts and oxides of heavy metals. Under these conditions, the conversion rate is only 2 to 3 percent per hour. Other oxidation catalysts are likewise well known, but in most instances, again, the conversation rate is low, as is the overall yield of the desired oxidation product.

It is an object of this invention, therefore, to provide a novel process for the oxidation of certain defined organic compounds whereby, in particular, the oxidation rate, or the selectivity for hydroperoxide formation, or both, may be increased. It is a further object of this invention to provide novel polymeric complexes useful as catalysts in this novel process.

SUMMARY OF THE INVENTION

It has now been found, in accordance with the present invention, that polymeric complexes formed between transition metal salts (including metals of the lanthanide series), and a thermally-condensed polyacrylonitrile polymer (hereinafter "polymer") are effective catalysts in the oxidation of those compounds containing activated carbon-hydrogen bonds as defined above. Certain of these novel catalysts, particularly those derived from metal salts of the transition metal series, are especially effective in selectively forming the hydroperoxides to the exclusion of hydroperoxides decomposition products.

DESCRIPTION OF THE INVENTION

The catalysts employed in the process of this invention, namely the transition metal salt polymer complexes, may generally be prepared by thermally condensing polyacrylonitrile in the presence of a metal salt to form an extensively conjugated aromatic nitrogen-containing aromatic polymer having metal ions associated therewith. The polyacrylonitrile may be thermally condensed by methods shown, for example, in Preparative Methods of Polymer Chemistry by W. R. Sorenson and T. W. Campbell, Interscience Publishers, page 170 (1961), whereby a selected amount of polymer is heated at about 200° to 400° C, preferably 200° to 275° C. Thus, the polyacrylonitrile of this invention is basically a high molecular weight homopolymer which, when heated, forms a compound comprised substantially of heterocyclic rings in accordance with the following structures:

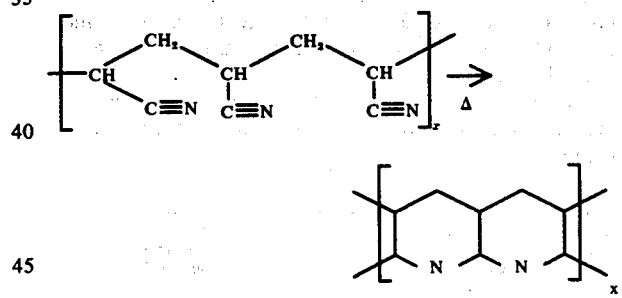

When this polymer is condensed by heat in the presence of a transition metal salt for about 2 to 10 hours, preferably 4 to 6 hours, using powdered polyacrylonitrile, there is obtained the desired catalyst. The ratio of polyacrylonitrile to metal salt is not at all critical and these two components may be mixed in almost any proportion, although desirably there should be an excess by weight of polymer present, preferable in the range of about 1 part polymer to 0.01 to 1 part by weight of metal salt.

These catalyst complexes are solid materials, even under the reaction conditions of this process, and, in fact, are insoluble in the oxidation product. They may, therefore, be readily recovered from the reaction mixture by simple filtration methods.

Many of these polymer metal complexes preferentially give yields of hydroperoxides to the exclusion of hydroperoxide decompositon products at conversion rates of at least about 3 to 8 percent per hour. In the case of those remaining metal complexes which yield little or no detectable amounts of hydroperoxides in the final product, but which do yield other oxidation products, this is because the hydroperoxides which are first formed are then rapidly decomposed by the catalyst complex itself to form aldehydes, alcohols, ketons or the like. This is to say, since the known mechanism for the autoxidation of alkyl aromatic compounds includes the homolytic cleavage of the first formed intermediate, i.e. the hydroperoxide, it is recognized that catalysts which accelerate this oxidation will also accelerate the decomposition of this intermediate. Hence it is possible to autoxidize the hydrocarbon to oxidized products without being able to detect the hydroperoxide intermediate becaue it is being decomposed to other oxidation products as rapidly as it is being formed. Therfore, the fact that no hydroperoxide is detected in the product does not mean it was not formed; it simply means that the catalyst is very effective in further converting this intermediate to aldehydes, ketones, alcohols, etc. In fact, the participation is so well established in the chemical literature that no other mechanical pathways are seriously considered. See, for example, G.A. Russel, J.A.C.S. 77, 4583–90, (1955); H. S. Blanchard, J.A.C.S. 82, 2014–21, (1959); J.A. Howard et al., Canadian Jour. Chem. 45, 785–792 ( 1966); inter alia.

Thus, it will be evident to those skilled in the art that the exact nature of the oxidation product can readily be determined by routine experimentation with various catalyst, but that in all cased it will be either an hydroperoxide and/or the decomposition products thereof as shown in the above-cited art, depending upon the exact catalyst composition chosen.

The metal salts used in forming the catalyst complexes are those derived from transistion of groups IIIB, IVB, VB, VIB, VIIB, VIIIB, IB, IIA or IIB, including the lanthanide metals. Of particular interest are such metals as Co, Ni, Mn, Cu, Ag, Pd, Pt, Ph, Mo, Cr, La, Cs, Nd and Gd.

The nature of the anion, X, is not critical, but may include any of the following inorganic or organic groups:

| | | | |
|---|---|---|---|
| CN$^-$ | cyanide | AsO$_3^=$ | arsenite |
| NC$^-$ | isocyanide | AsO$_4^=$ | arsenate |
| CN$_2^-$ | cyanamide | C$_2$H$_3$O$_2^-$ | acetate* |
| OCN$^-$ | cyanate* | C$_4$H$_4$O$_6^-$ | tartrate |
| CNO$^-$ | isocyanate* | C$_7$H$_5$O$_2^-$ | benzoate |
| ClO$^-$ | chlorite | B$_4$O$_7^-$ | tetraborate |
| ClO$_2^-$ | chlorate | BrO$_3^-$ | bromate |
| SCN$^-$ | thiocyanate | Cr$_2$O$_7^-$ | dichromate |
| CNS$^-$ | isothiocyanate | F$^-$ | fluoride |
| SeCN$^-$ | selenocyanate | CH$_2$O$^-$ | formate |
| S$_2$O$_3^-$ | thiosulfate | SeO$_3^-$ | selenide |
| SO$_2^-$ | sulfite | SeO$_4^-$ | selenate |
| SO$_4^-$ | sulfate | C$_6$H$_5$O$^-$ | phenoxide |
| S$^-$ | sulfide | C$_2$O$_4^-$ | oxalate* |
| HS$^-$ | hydrosulfide | O$^-$ | oxide |
| TeCN$^-$ | tellurocyanate | TeO$_3^-$ | tellurite |
| OCl$^-$ | oxychloride | AsS$_3^-$ | thioarsenite |
| OH$^-$ | hydroxide | AsS$_4^-$ | thioarsenate |
| NO$_2^-$ | nitrite* | Cl$^-$ | chloride* |
| PO$_3^=$ | phosphite | Br$^-$ | bromide* |

-continued

| | | | |
|---|---|---|---|
| PO$_4^=$ | phosphate* | NO$_3^-$ | nitrate* |
| CrO$_4^-$ | chromate | CO$_3^-$ | carbonate* |
| BO$_3^=$ | borate | ClO$_4^-$ | perchlorate* | in which those marked with an asterisk are most preferred.

As mentioned hereinabove, the oxidation products of the instant process are hydroperioxides, or the decomposition products therof, i.e. alcohols, ketons, aldehydes, epoxides or mixtures thereof. Of these various products, maximization of the formation of th hydroperoxides is generally preferred inasmuch as those compounds useful as intermediates in the preparation of such products as phenols, naphthols, acetone and the like, while those derived from, e.g., the olefin hydroperoxides, are useful in facilitating the drying capabilities of polymers, i.e., they are useful as siccative agents.

The components which may be oxidized in accordance with the present invention are, as mentioned above, those organic compounds containing activated carbon-hydrogen bonds. That is to say, they include those hydrogen-containing carbon atoms, and particularly methylene and methine groups, which are adjacent certain activating group. These activating groups includes such groups as —CH=CH—, —OR, —NO$_2$, halo, phenyl, and the like, where R is alkyl or cycloalkyl.

Included amongst the starting materials which are of particular use in this process are any straight or branched chain unsaturated olefine having at least one hydrogen atom of the α-carbon atoms, such as octene-1, and th like as well as cyclic olefins having at least one hydrogen atom on the α-carbon atom, such as cyclohexane, cyclooctadiene, α-pinene, dl-limonene and the like. These olefins may contain substitutent groups which are non-reactive under the conditions of this process, as for example, ester, halo, nitro, alkyl or like groups which remain as substituents of the final product.

Also included as preferred starting material in this process are secondary and tertiary alkylaromatic hydrocarbons having the structural formula:

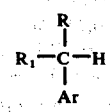

wherein R is lower alkyl; R$_1$ is lower alkyl or hydrogen; Ar is a substituted or unsubstituted aromatic nucleus such as phenyl or naphthyl; and wherein R and R$_1$ may be the same or different alkyl groups. The aromatic nucleus may be substituted by such groups as lower alkyl, lower alkoxy, halo, nitro or cyano radicals. Preferably, the secondary and tertiary alkylaromatic hydrocarbon is represented by such compounds as cumene, ethylbenzene, or sec.-butylnaphthalene, although it is understood that compounds such as n-butylbenzene, sec.-butylbenzene, isopropylnaphthalene and the like may also be employed. The lower alkyl groups may contain from 1 to 12 carbon atoms. It will be understood that by "secondary" is meant those compounds of the formula:

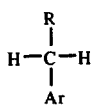

as defined above; while "tertiary" is intended to signify those compounds of the formula:

as defined above, where $R_1$ is alkyl.

The process of this invention is conveniently carried out by the rapid passage of air or oxygen through a suitable reactor, to which has first been added the starting material, although solvents which are inert to the reaction of proxidation may likewise be employed.

The air or oxygen should be brought into intimate contact with the liquid phase with vigorous agitation either mechanically by the use of high speed stirrers, or by aceration using suitable nozzles or the like.

Mechanical agitation has been found to be particularly effect in those cases where the rate at which the oxygenating gas is introduced into the reactor is low, i.e., below about 3 liters per hour. Thus, for example, when the air is merely introduced at the surface of the reaction mixture, agitation by a commercially available reciprocating disc type stirrer (e.g., "Vibro-Mixer," Chempec Company, Inc., Hoboken, N.J.) has been found to increase the rate of oxidation per hour by as much as four-fold over what is obtained with lesser amounts of agitation.

Alternatively, these increased rates may similarly be achieved, and mechanical agitation substantailly or entirely dispened with by appreciably increasing the rate at which air or oxygen is introduced into the reaction medium. This is preferably accomplished by bubbling the oxygenating gas through the reaction mixture, vigorously, desirably in such a manner as to insure maximum dispersal of the gas through the medium, as for example, by using fritted glass discs or the like. Depending upon the amount of liquid medium involved, the rate of oxygenating gas may generally vary from about 3 to 300 liters per hour.

The amount of catalyst employed will vary depending upon the nature of the catalyst itself. In general, however, from about 0.01 to 5.0 parts by weight of catalyst per 100 parts per substrate, and preferably from 0.2 to 1.0 parts per 100 parts has been found to be satisfactory.

The rate of input of oxygen or air will likewise vary depending upon the reaction temperature and pressure employed. There should be provided an amount at least theoretically sufficient to convert the alkyl aromatic compound to the corresponding hydroperoxide, and preferably an excess of this amount. In general, a flow rate ranging from 0.5 to 300 liters per hour is sufficient for most conversions, and preferably at least 3 liters per hour as described above. While the reaction is preferably carried out at atmospheric pressure, it is possible to employ an oxygen pressure of from about 0.2 to 50 atmospheres, and preferably about 1 to 10 atmospheres. At these higher pressures the oxidation rate is found to increase substantially when the polymeric complexes are employed, and particularly those catalysts which are selective for hydroperoxide formation.

The reaction temperature may range from about 80° to 200° C, and preferably from 90° to 150° C.

The reaction is generally run for from half an hour to 10 hours, depending upon the amount of substrate employed and the degreee of conversion desired. When, however, an hydroperoxide is the principal product being formed, it is desirable that the reaction be terminated after a period of 1 to 6 hours at which point the reaction rate usually begins to taper off.

Advantageously, small amounts of an hydroperoxide, preferably one corresponding to the desired product, may be introduced into the reaction medium to act as a reaction initiator. Thus, for example, when cumene is being oxidized, it has been found to be advantageous to add small amounts of cumyl hydroperoxide in order to further accelerate the initial rate of reaction. The amount of hydroperoxide to be added is not critical, but 0.1 percent to 1.0 percent by weight of the starting material is preferred. It should be understood, however, that the addition of any such initiator will not change the nature of the product that would otherwise be obtained; the initiator serves only to reduce the induction time of the reaction.

The resulting products are readily recovered from the reaction medium by conventional methods. Thus, for example, an hydroperoxide may be conveniently recovered by isolating it as its sodium salt by addition of concentrated aqueous NaOH to the reaction product, followed by separation and drying of the hydroperoxide salt.

In the following examples, unles otherwise noted, both rate of conversion of the starting material and selectivity of the catalyst for converting the starting material to the corresponding hydroperoxide were measured. To measure rate of conversion, regardless of the nature of the oxidation product, the amount of oxygen uptake in a closed system was used; to measure the amount of hydroperoxide formed, samples of the reaction medium were periodically withdrawn and iodometrically titrated to determine the hydroperoxide content. On the basis of both these figures the selectivity of any given catalyst for the formation of hydroperoxide could then be routinely determined.

EXAMPLE 1

Preparation of Nickel-condensed Polyacrylonitrile Catalyst 2.7 gms. of powdered polyacrylonitrile was intimately admixed with 0.3 gms. (10 wt. percent) of nickel chloride. The mixture was poured into a heavy-walled glass tube sealed at one end, and the tube immersed in a Woods-metal bath. A thin tube delivering a slow stream of air was placed just above the surface of the mixture. The mixture was then heated to 240° C for 6 hours, during which time it was occasionally agitated mechanically. On cooling the catalyst was recovered directly from the tube, ready to use.

In accordance wih the foregoing procedure, but substituting copper chloride and cobalt chloride, respectively, for nickel chloride, there was obtained the corresponding copper complex and cobalt complex of thermally-condensed polyacrylonitrile.

By substituting other appropriate metal salts, as desired, and following the foregoing procedure other polymer metal complexes may likewise be prepared.

EXAMPLE 2

Cumene Oxidation Using Nickel-condensing Polyacrylonitrile catalyst

In a 50 ml. round bottom, 3-nickel flask fitted with a serum cap, reciprocating stirring and a gas inlet tube which is connected to an oxygen filled buret, were placed 12.0 g. (0.10 mole) of cumene, 0.2 cc (~0.001 mole) of cumene hydroperoxide, and 0.060 g. of the thermal fusion product from a mixture of nickel chloride and polyacrylonitrile. The flask was swept with oxygen, placed in an oil bath at 100° C, stirring initiated, and opened to the gas buret. The absorption of oxygen was measured as a function of time. Periodically small aliquots (0.50 g.) were withdrawn and titrated to determine the cumene ahydroperoxide content of the reaction mixture. In this way it was found that the oxidation proceeded to give high selectivities for the production of hydroperoxide.

Table 1

| Time | % Conversion | % Hydroperoxide | % Molar Selectivity |
|---|---|---|---|
| 1 hr. | 3.2 | 3.4 | 100 |
| 2 hr. | 9.3 | 8.6 | 93 |
| 3 hr. | 14.2 | 12.6 | 89 |
| 4 hr. | 17.6 | 16.3 | 93 |

The first hour rate of oxidation is not unusual and was apparently due to some induction period. The 6 percent conversion observed during the second hour was considerably faster than that observed in the absence of any catalyst. More significant is the high (~90%) selectivity for hydroperoxide formation.

In accordance with the foregoing procedure, but substituting ethylbenzene or sec.-butylbenzene for cumene, there is obtained ethylbenezene hydroperoxide or sec.-butylbenzene hydroperoxide respectively.

EXAMPLE 3

Cumene Oxidation Using Copper-condensed Polyacrylonitrile Catalyst

An oxidation similar to Example 2 was carried out using 0.060 g. of the product obtained by thermal treatment of polyacrylonitrile and copper(II) chloride. The following results were observed:

Table 2

| Time | % Conversion | % Hydroperoxide | % Molar Selectivity |
|---|---|---|---|
| 1 hr. | 8.4 | 10.1 | 100 |
| 2 hr. | 15.8 | 15.6 | 99 |
| 3 hr. | 20.2 | 20.4 | 100 |

With this catalyst the rate was enhanced over Example 2, and the selectively for hydroperoxide was excellent.

In accordance with the foregoing procedure, but substituting isopropylnaphthalene or sec.-butylnaphthalene for cumene, there is obtained the corresponding isopropylnaphthalene hydroperoxide or sec.-butylnaphthalene hyroperoxide respectively.

EXAMPLE 4

Cumene Oxidation Using Cobalt-condensed Polyacrylonitrile Catalyst

An oxidation similar to that of Example 2 was carried out using as the catalyst 0.060 g. of the product obtained by thermal treatment (~250° C) of an intimate mixture of cobalt (II) chloride and polyacrylonitrile. The following results were obtained.

Table 3

| Time | % Conversion | % Hydroperoxide | % Molar Selectivity |
|---|---|---|---|
| 1 hr. | 6.0 | 6.4 | 100 |
| 2 hr. | 9.9 | 10.3 | 100 |

This example illustrates the high selectivity for hydroperoxide shown by this catalyst. In most similar oxidations using a cobalt-derived catalyst (e.g., cobalt napthenate or cobalt resinate) there was observed a very low (50%) selectivity for hydroperoxide formation.

In accordance with the foregoing procedure, but substituting cyclohexane, 1-octene, or cyclooctadiene, for cumene, there is obtained the corresponding cyclohexane hydroperoxide, 1-octene hydroperoxide or cyclooctadiene hydroperoxide, respectively.

EXAMPLE 5

Following the procedure of Example 2, but using instead of cumene 8.2 g. (0.1 mole) of cyclohexane, and 0.06 g. of copper II polyacrylonitrile chloride, there is obtained during the first 2 hours a 7.1% rate or oxidation. After the first hour the selectivity to cyclohexane hydroperoxide is 90%; after the second hour the selectivity falls to 74%. Cyclohexanol and cyclohexenone, products of the further decompositon of cyclohexane hydroperoxide comprises the remainder of the reacted material.

EXAMPLE 6

Following the general procedure of Example 2, but using 10.8 g. of 1,5 cyclooctadiene, and 0.060 g. of the thermal fusion product from a mixture of manganese chloride and polyacrylonitrile, there is obtained after one hour of oxidation a 12% conversion of the diolefin. Titration of the reaction product afforded a 50% yield of hydroperoxide, the ramainder of the reaction product comprising cyclooctadienone and cyclooctadienol, i.e., further decomposition products of the first formed hydroperoxide.

In a similar experiment, but using 13.6 g. d-limonene as the substrate, a 15% conversion of the olefin is observed during the first hour with a high yield of hydroperoxide.

EXAMPLE 7

Following the general procedure of Example 2, but using as the catalyst 60 mg. of the thermal fusion product obtained from a mixture of $LaCl_3$ and polyacrylonitrile, there is obtained after 1 hour a 7.0% conversion of the cumene. The yield of cumene hydroperoxide is 100%.

In a similar experiment using isopropylnaphthalene as the substrate a high yield of hydroperoxide is obtained.

In a similar experiment using freshly distilled pinene as the substrate, pinene hydroperoxide is obtained in good yield.

The invention claimed is:

1. In the process for the catalytic oxidation of aliphatic or alicyclic olefins having at least one hydrogen atom on the α-carbon atom, said olefins having 3 to 18 carbon atoms, or secondary or tertiary alkylaromatic hydrocarbons of the formula

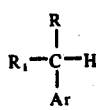

wherein R is lower alkyl; $R_1$ is lower alkyl or hydrogen; and Ar is an aromatic nucleus selected from the group consisting of phenyl and naphthyl, in the presence of air or oxygen at a temperature of from about 80° to 200° C to form hydroperoxides, the decomposition products thereof, or mixtures of the same, the improvement wherein the catalyst is a polymeric complex formed from a thermally condensed polyacrylonitrile and a transition metal salt, wherein said transition metal is from Group IB, IIB, IIIB, IVB, VB, VIB, VIIB, VIIIB, or IIA of the Periodic Table and wherein the ratio of said catalyst to said olefin or alkylaromatic hydrocarbon is from about 0.01 to 5.0 parts by weight of catalyst per 100 parts by weight of olefin or alkylaromatic hydrocarbon.

2. The process according to claim 1 wherein the metal of the metal salt is of the lanthanide or actinide series of the Periodic Table.

3. The process according to claim 1 wherein the alkylaromatic compound is cumene and the product consists substantially of cumyl hydroperoxide.

4. The process according to claim 1 wherein the oxidation is carried out in the added presence of an hydroperioxide initiator.

5. The process according to claim 1 wherein the ratio of catalyst to olefin is in the range of from 0.2 to 1.0 parts by weight of catalyst per 100 parts of olefin.

6. The process according to claim 1 wherein the reaction is carried out under vigorous agitation.

7. The process according to claim 1 wherein the oxygen is introduced at a rate of from about 0.5 to 300 liters per hour.

8. The process according to claim 1 wherein the oxidation is carried out at an oxygen pressure of from 1 to 50 atmospheres.

9. The process according to claim 1 wherein the anion is a bromide, chloride, carbonate, nitrate or perchlorate.

10. The process according to claim 1 wherein the anion is a cyanide, cyanate, isocyanate, nitrite, phosphate, acetate, or oxalate.

11. The process according to claim 1 wherein the hydroperoxide decomposition products are alcohols, aldehydes, ketones, or mixtures thereof.

12. The process according to claim 1 wherein the salt is a nickel, copper, or cobalt salt.

13. The process according to claim 1 wherein the thermally-condensed polyacrylonitrile metal salt catalyst is formed by the heating of an excess by weight to the metal salt of the homopolymeric polyacrylonitrile at temperatures of from about 200° to 400° C in the presence of said metal salt.

* * * * *